(12) United States Patent
Santelli et al.

(10) Patent No.: US 6,336,462 B1
(45) Date of Patent: Jan. 8, 2002

(54) EYEBROW SHAPING AND WAXING TEMPLATE

(76) Inventors: Gianna Santelli, 50 Old Mill Road, Oakville, Ontario (CA), L6J 7W1; Bonita J. Lischka, 50 Parade Square, Scarborough, Ontario (CA), M1C 3T6

( * ) Notice: Subject to any disclaimer, the term of this patent is extended or adjusted under 35 U.S.C. 154(b) by 0 days.

(21) Appl. No.: 09/783,003

(22) Filed: Feb. 15, 2001

(51) Int. Cl.⁷ .................. A45D 40/30; A45D 29/00
(52) U.S. Cl. .................. 132/319; 132/216; 132/285
(58) Field of Search .................. 132/319, 218, 132/216, 285, 275; 607/95; 601/1, 116; 101/35, 126

(56) References Cited

U.S. PATENT DOCUMENTS

| | | | | |
|---|---|---|---|---|
| 5,052,418 A | * | 10/1991 | Miller | 132/319 |
| 5,470,351 A | * | 11/1995 | Ross et al | 607/95 |
| 5,836,998 A | * | 11/1998 | Mueller et al. | 607/95 |
| 5,928,797 A | * | 7/1999 | Vineberg | 428/500 |
| 6,161,554 A | * | 12/2000 | Dunlap-Harris | 132/216 |

* cited by examiner

*Primary Examiner*—John J. Wilson
*Assistant Examiner*—Robyn Kieu Doan
(74) *Attorney, Agent, or Firm*—Marks & Clerk

(57) ABSTRACT

A template may be formed from such as surgical tape, having an opening cut therein in the shape of an eyebrow. The template may have a low-tack adhesive coating on one side, or a depilatory coating, or one of each on both sides of the substrate. When used for eyebrow shaping, the adhesive side is adhered to the skin, and colouring is applied through the opening. When used for waxing, the depilatory coating is applied to the region around the shape of the eyebrow to be left after the depilation procedure. The depilatory coating may be a heat-activated composition, or a pressure-activated composition. The templates may be provided in pairs, in rolls of groups of pairs.

18 Claims, 1 Drawing Sheet

EYEBROW SHAPING AND WAXING TEMPLATE

FIELD OF THE INVENTION

This present invention applies to the field of cosmetics and beauty treatment as they apply particularly to the eyebrows of the human face. In particular, the present invention provides templates which may be used for shaping the eyebrows by colouring through an opening in the template; or in another embodiment, the present invention provides a template for applying a depilatory composition to the face in the region surrounding an eyebrow so as to perform a depilation procedure; or in yet another embodiment of the present invention, a template is provided having an adhesive coating on one side for performing an eyebrow shaping procedure, and a depilatory composition on the other side for performing a depilation procedure.

BACKGROUND OF THE INVENTION

Many people, mostly female but not exclusively, are concerned about the shape and appearance of their eyebrows. This may mean simply the application of eyeliner or other colouring agent to enhance the appearance of the eyebrow; and in some instances, to increase the width or length of the eyebrow so as to appear more prominent. Indeed, in some instances, there are persons who have very little hair in the eyebrow region of their face, over the orbital arch of the frontal bone of the face, and those persons will want to define an eyebrow shape so as to normalize their appearance.

In other instances, many persons have too much hair, or hair in the wrong place for the desired shape of the eyebrow, and such persons undergo depilation procedures of various sorts. One such procedure is that of electrolysis, whereby the hair is removed using an electrical electrolysis apparatus. Such procedure is painful, may generally leave unsightly swelling or redness, and is temporary at best. More permanent depilation procedures involve the application of depilatory waxes in the region surrounding the eyebrow—or that portion of the eyebrow which is intended to remain after the depilation procedure—so as to remove the unwanted hair by literally grasping the hair and pulling it from the face by the roots. Waxing procedures can also be uncomfortable, especially if waxes are employed which must be softened at temperatures above 55° C., thereby causing discomfort and possibly minor irritation resulting, again, in redness or swelling. Moreover, if the depilatory composition is put into the wrong place, then more hair may be removed than is desired. Typically, depilation waxes are applied using an instrument such as a small spatula.

Some depilatory strips are known, but they require to be carefully put into place, so as not to remove hair that is intended to be left.

The use of templates to serve both purposes of eyebrow shaping and eyebrow waxing quite surprisingly presents itself, it being unknown hither to in the professional beauty salon business to employ the use of templates particularly for eyebrow waxing depilation procedures.

Moreover, it is possible for the ordinary consumer to employ eyebrow shaping templates or eyebrow waxing templates of the sort taught herein, without having to go to a professional cosmetic or beauty salon.

Quite surprisingly, it has been discovered that if a template is provided on a flexible substrate such that it will conform to the orbital arch of the frontal bone of the human face, then an eyebrow shaping procedure or an eyebrow waxing depilation procedure can be easily and effectively carried out, either by a professional cosmetician, or by the consumer in her or his home, studio, or dressing room—it being recognized that actors and/or television personalities in particular may require constant eyebrow care.

DESCRIPTION OF THE PRIOR ART

The prior art provides a variety of depilatory procedures and other depilatory compositions, and it provides a plurality of very complicated templates or stencils for use in eyebrow colouring procedures. The depilatory waxes which are found in the prior art may be used for eyebrow waxing procedures, but are more often generally intended for depilation procedures on the legs, face, and other parts of the human body as well as—or instead of—specifically in the eyebrow region.

Of course, probably the most common manner in which the shape of the eyebrows may be changed is simply by plucking or tweezing the unwanted hairs away from the face. Such a procedure is slow and tedious, and is quite likely to cause secondary minor infection where the hairs have been pulled from the skin.

British Patent Specification 1,348,760 published Mar. 20, 1974 to Dupuy teaches a depilatory wax which is a multi-part composition. The first part is a resinous substance having a melting point in the range of 85° C. and consisting of 75% to 80% by weight colophane and 20% to 25% by weight of paraffin wax. The second part is a resinous substance having a melting point in the range of 77° C. and consisting of 70% to 75% by weight colophane and 25% to 30% by weight paraffin wax. The third part is a resinous substance having a melting point of 80° C. and comprising about 66% by weight colophane with the remainder being paraffin wax and spermaceti fat. At least one mineral oil or other oil known in the cosmetic composition industry is also employed. The wax is said to have a viscous state in the range of 50° C. to 60° C. The wax may also contain secondary additives such as colouring matters, or finely dispersed inert solid fillers such as alumina.

Canadian Patent 1,166,577 issued May 1, 1984 to Fuentes teaches a depilatory wax which comprises 100 parts of tree resin, 10 to 20 parts of beeswax, 8 to 13 parts of castor oil, and 10 to 20 parts of calcium carbonate. The wax is applied using a stick applicator after it has been warmed to a temperature where it just begins to drip from the applicator, and after application it is rapidly pulled away from the skin so as to remove the hair with it.

U.S. Pat. No. 5,186,190 issued Feb. 16, 1993 to Hirzel teaches an eyebrow stencil kit which comprises a pair of wing-shaped stencils which are connected by a nut and bolt that is placed in the middle of the forehead when the stencil kit is in use. One or more eyebrow cut-outs are provided, and eyeliner and other colouring agent is applied through the stencil cut-outs. The stencil is held in place during use by a stretchable headband and clip arrangement secured around the head.

Another stencil arrangement which is secured around the head by elastic bands is taught in Grenevitch et al U.S. Pat. No. 5,662,129 issued Sep. 2, 1997. Here, a template holder is put into place, and a series of different templates may be retained in the template holder, and simulated eyebrows are stencilled in place on the face of the user. The patent also suggests that the periphery of a template opening can be traced and after the apparatus is removed, the eyebrow hairs outside the traced area can be plucked.

Naggiar U.S. Pat. No. 5,698,187, issued Dec. 16, 1997, teaches a cold wax depilatory composition which comprises a mixture of maltodextrin having a dextrose equivalent of from about 5 to about 36, sucrose, water, and citric acid. Here, the mixture is heated so as to dissolve the solute materials and is then cooled to become a soft and pliant composition which is then manually applied to the skin. The hairs of the skin adhere to the composition such that, when it is drawn away, the hairs are removed. The composition has a waxy consistency when it has been cooled to a soft and pliant composition for application to the skin.

Helprin U.S. Pat. No. 5,860,433, issued Jan. 19, 1999, teaches an eyebrow forming template which has a backing sheet, and one or more sets of right and left eyebrow templates. The templates are provided with an adhesive so to allow them to be retained on the backing sheet and so as to allow them to be placed and retained on the eyebrow area of the user. Removable right and left eyebrow shapes are formed in the templates and are removed before applying the templates to the eyebrow area so that the shape may be filled in using any appropriate eyebrow pencil, eyebrow liner, powder, or similar product. The material of the template or stencil, and of the peel off adhesive, are all materials which are approved by the FDA for external eye area treatment.

Japanese Patent Publication 59029611, published Feb. 16, 1984 by Isehan K K teaches a depilatory wax product which has 50% rosin, 25% beeswax, 15% paraffin, and 10% Vaseline, together with some perfume. It has a melting temperature of about 60° C. to 65° C., and is easily melted by being placed in a cup which is placed into a water bath.

Japanese Patent Publication 61212513 published Sep. 20, 1986 in the name of Kanebo Ltd. teaches a pressure-sensitive adhesive depilatory which has an analgesic effect to suppress the pain which is caused by peeling of the depilation plaster away from the skin. In particular, analgesic is employed using an extract of the dried root and rhizome of the species *Asiasarun sieboldi*. The depilatory is a pressure-sensitive adhesive which may be a thermoplastic elastomer, a depilatory wax, or a depilatory jelly.

Japanese Patent Publication 08089341, published Apr. 9, 1996 in the name of Fujiwara teaches an eyebrow shaping sheet which has a shape cut into it to be placed against the forehead or temple. The sheet is stabilized on the face simply by being pressed against the face by hand, and the eyebrow is drawn using a powder or pencil eyebrow make-up. The sheet of the stencil may be paper, plastic, vinyl, or cellophane.

Japanese Patent Publication 10108730, published Apr. 28, 1998 in the name of Kose Corporation, also teaches a template for make-up of the eyebrow. Here, the template is one which folds, and is secured in place by a couple of adhesive positioning parts. One half of the template has a wider shaping hole than the other. The wider shaping hole is employed first so as to paint the general eyebrow shape, then the template is folded and a relatively dark colour is painted through the narrow hole.

Another product in the Canadian market at the time of filing the present application is sold in association with the trade-mark SUDDEN CHANGE®, and comprises pairs of so-called eyebrow shapers; which, are a set of pre-cut shapers that are placed over and under the eyebrows for depilation purposes. However, notwithstanding that the literature suggests a waxing step, the shapers are, in fact, coated on one side thereof with a high tack adhesive, and are mounted on a release backing.

SUMMARY OF THE INVENTION

The present invention provides templates which may find themselves having three different embodiments. The first is an eyebrow shaping template, the second is an eyebrow waxing template, and the third is both an eyebrow shaping template and an eyebrow waxing template. As will be noted hereafter, each template in keeping with the present invention employs the use of a substrate having at least one coating thereon. That coating may be a low-tack non-allergenic adhesive, or it may be a depilatory coating. In the case where the invention provides both an eyebrow shaping template and an eyebrow waxing template, both of the low-tack non-allergenic adhesive coating and the depilatory coating are found, one on each side of the substrate.

Because the human face is essentially symmetrical, the left and right eyebrows are essentially mirror images one of the other. Thus, two-sided templates in keeping with the present invention will be employed for either the right eyebrow or the left eyebrow, depending on whether it is the low-tack non-allergenic adhesive coating or the depilatory coating which is facing and in contact with the skin of the face in the region surrounding that respective left or right eyebrow.

The present invention provides an eyebrow shaping template to be applied to the eyebrow area of the human face for defining an area for colouring a desired shape of a left or right eyebrow, the template comprising a substrate which has a first side and a second side, and a low-tack non-allergenic adhesive coating on one or the other of the first and second sides of the substrate. The adhesive coating permits for temporary adhesion of the template to the skin of the human face.

An opening is formed through the adhesive coating and the substrate, the shape of the opening being the desired shape for a left eyebrow or a right eyebrow.

The substrate is flexible; and it is non-stretchable so as to maintain its shape and the shape of the opening therein when the template is in use.

The present invention provides for an eyebrow shaping template set, which set comprises a pair of eyebrow shaping templates as noted above.

One of the pair of templates has an opening formed therein for colouring a left eyebrow when placed in the left eyebrow area of a human face, with the adhesive coating thereon in contact with the skin of the face. The other of the pair of templates has an opening formed therein for colouring a right eyebrow when placed in the right eyebrow area of a human face, with the adhesive coating thereon in contact with the skin of the face.

In keeping with another provision of the present invention, each of the pair of eyebrow shaping templates in the eyebrow shaping template set has an opening formed therein which is chosen from a plurality of different shapes, for colouring different shaped eyebrows.

The substrate may be chosen from the group consisting of surgical tape, paper, vinyl, cellulose, polyethylene, tightly woven synthetic fibres, tightly woven natural fibres, and combinations and mixtures thereof.

The eyebrow shaping template set of the present invention may be one of a plurality of similar pairs of eyebrow shaping templates, each of which has first and second ends, and which are removable attached one to another at their respective first and second ends. Thus, the plurality of pairs of eyebrow shaping templates may be formed into a roll, for dispensing one pair of eyebrow shaping templates at a time.

Typically, when the eyebrow shaping templates are rolled in a plurality of sets thereof, a release film is placed over the low-tack non-allergenic adhesive coating so as to keep one layer of the rolled template sets from adhering to another layer of the rolled template sets.

The opening which is formed in each eyebrow shaping template may be formed by stamping the material of the template, whereby a chad is formed in the shape of the opening. Especially when there is a release film placed over the low-tack non-allergenic adhesive coating, the chad may be removed and applied to an eyebrow for masking the eyebrow when further procedures will follow in the region surrounding the eyebrow.

Another embodiment of the present invention provides an eyebrow waxing template for depilation of an area surrounding a left or right eyebrow on the human face. In this case, the eyebrow template also comprises a substrate having a first side and a second side, and a depilatory coating on one of the first or second sides. The coating is intended for placement against the skin and against any unwanted hair in the eyebrow region of a human face.

There is, again, an opening formed through the depilatory coating and the substrate. The opening has a desired shape of a left eyebrow or a right eyebrow to remain in the eyebrow area of a human face following a depilation procedure.

The substrate is flexible, and is non-stretchable so as to maintain its shape and the shape of the opening therein when the template is in use.

The depilatory coating is chosen from the group which consists of heat-activated depilatory compositions, pressure-activated depilatory compositions, and compositions thereof.

As before, an eyebrow waxing template set is provided in keeping with the present invention, by the provision of a pair of eyebrow waxing templates as described above. One of the pair of templates has an opening therein for placement over the left eyebrow of a human face during a depilation procedure in the region of that left eyebrow; and the other of the pair of templates has an opening therein for placement over the right eyebrow of the human face during a depilation procedure in the region of that right eyebrow.

As above, each of the pair of eyebrow waxing templates may have an opening formed therein which is chosen from a plurality of different shapes.

The substrate for the eyebrow waxing template of the present invention may be the same as described above. Also, a plurality of pairs of eyebrow waxing templates in keeping with the present invention may be wound in a roll, also as described above.

The eyebrow waxing depilatory coating may be a heat-activated depilatory composition which may be chosen from the group of such compositions that consists of a low melting point depilatory wax which includes a naturally occurring resinous substance, a low melting point depilatory wax which includes paraffin wax, a low melting depilatory wax which includes sucrose and maltodextrin, and mixtures thereof. The depilatory coating is heat-activatable by being temporarily exposed to a source of radiant heat, or by being placed in contact with steam or a heated liquid. Also, the depilatory coating may be a pressure-sensitive depilatory composition chosen from the group of such compositions which consists of styrene-isoprene-styrene copolymers, hydrogenated rosins, depilatory jellies which include a starch syrup, and mixtures thereof.

Yet a further embodiment of the present invention provides for an eyebrow shaping and waxing template for conducting either of an eyebrow colouring procedure to either of the left eyebrow or the right eyebrow of a human face, or a depilation procedure of the hair surrounding the eyebrow in the region of the right eyebrow or the left eyebrow of a human face.

The eyebrow shaping and waxing template also comprises a substrate, which has a first side and a second side.

A low-tack non-allergenic adhesive coating is applied on the first side of the substrate, for temporarily adhering to the skin of the human face; and a depilatory coating is applied on the second side of the substrate, for placement against the skin and any unwanted hair in the eyebrow region of a human face.

An opening is formed through the adhesive coating, the substrate, and the depilatory coating, where the opening has a desired shape of an eyebrow area to be coloured or of the eyebrow which is intended to remain in the eyebrow area of a human face following a depilation procedure.

As before, the substrate is flexible, and is non-stretchable so as to maintain its shape and the shape of the opening therein when the template is in use. Also, as before, the depilatory coating may be chosen from the group which consists of heat-activated depilatory compositions, pressure-activated depilatory compositions, and combinations thereof.

An eyebrow shaping and waxing template set may be provided in keeping with the present invention, for colouring a desired shape of both a left and a right eyebrow on a human face, or for depilation of the area surrounding each of the left eyebrow and the right eyebrow of a human face—the set thereby taking advantage of the symmetry of the human face. The eyebrow shaping and waxing template set comprises a pair of eyebrow shaping and waxing templates as described above.

One of the pair of eyebrow shaping and waxing templates has an opening formed therein for colouring a left eyebrow when placed in the left eyebrow area of a human face with the adhesive coating on the first side of the substrate being in contact with the skin of the face in the region of the left eyebrow. Alternatively, that particular one of the pair of eyebrow shaping and waxing templates may be intended for placement over the right eyebrow of a human face during a depilation procedure in the region of the right eyebrow when the depilatory coating on the second side of the substrate is placed against the skin and any unwanted hair in the right eyebrow region of the human face.

Likewise, the other of the pair of eyebrow shaping and waxing templates may be intended for use in colouring a right eyebrow, or for placement over the left eyebrow of a human face during a depilation procedure in the region of the left eyebrow.

As before, each of the eyebrow shaping and waxing templates in the set may have an opening formed therein which is chosen from a plurality of different shapes, for colouring different shaped eyebrows, or for use during any depilation procedure in the region of the left or right eyebrow, each having a desired shape.

The substrate of the eyebrow shaping and waxing template of the present invention may be as described above.

Also, as noted above, pluralities of pairs of eyebrow shaping and waxing templates in keeping with the present invention may be provided in a roll thereof.

Typically, when there is a plurality of eyebrow shaping and waxing templates which are provided in a roll, a release film is placed over the low-tack non-allergenic adhesive coating on the first side of the substrate, so as to preclude adhesion of the adhesive coating on one layer of the roll against the depilatory coating on the adjacent layer of the roll.

The depilatory coating on the second side of the substrate of an eyebrow shaping and waxing template in keeping with the present invention, may be a heat-activated depilatory composition, a pressure-activated depilatory composition, or a combination thereof.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

The novel features which are believed to be characteristic of the present invention, as to its structure, organization, use and method of operation, together with further objectives and advantages thereof, will be better understood from the following discussion.

For purposes of the following discussion, the term eyebrow treatment template will be used to mean either an eyebrow shaping template, an eyebrow waxing template, or an eyebrow shaping and waxing template. The structure of all such templates is essentially the same, except that an eyebrow shaping and waxing template has a coating on both sides of the substrate.

Figure 1:
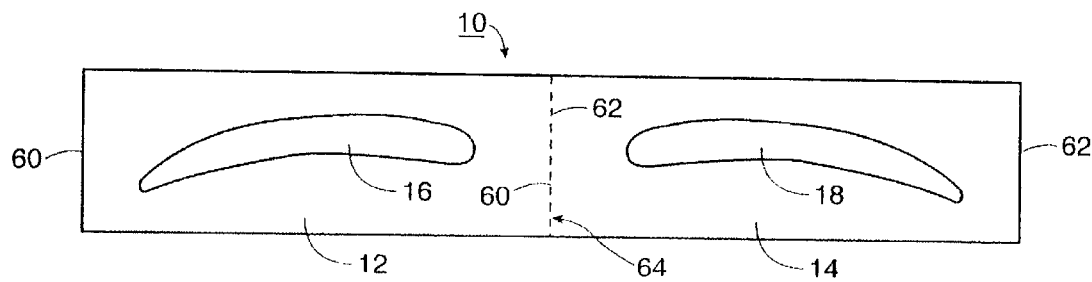
FIG. 1 shows a typical set of eyebrow treatment templates in keeping with the present invention.

A set of eyebrow treatment templates 12 and 14 is shown at 10 in FIG. 1. Each of the templates 12 and 14 has a respective opening 16 and 18 formed therein.

It will be evident that the openings 16 and 18 may be used for either the right eyebrow or the left eyebrow, depending on whether the upper surface or the lower surface of the eyebrow treatment template, as seen in FIG. 1, is the surface which is in contact with the skin of the human face at the orbital arch of the frontal bone thereof. This is the eyebrow region of the human face; and the eyebrows may conform with and be aligned along the orbital arch, or they may be spaced somewhat above the orbital arch. Moreover, many persons wish to simulate an eyebrow shape, or define an eyebrow shape, in an area of the forehead above the eye, which area may not necessarily be the area where that person's eyebrows actually have grown.

Accordingly, in the following discussion, there is no indication as to whether a template is a right template or a left template for use with the right eyebrow or left eyebrow, because it depends on which side of the template is placed against the skin of the human face in the eyebrow area.

Figure 2:
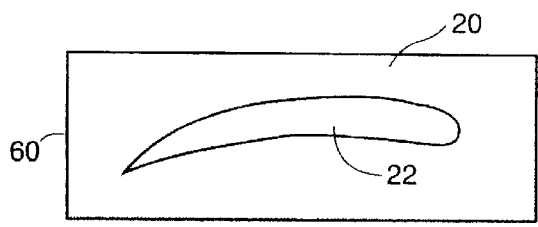
FIG. 2 shows a single template having a different shape of opening than the openings in the templates of the set of FIG. 1.
Figure 3:
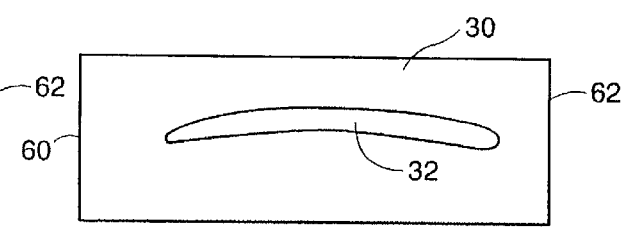
FIG. 3 shows a single template having yet a further different shape of opening than the openings in the templates of FIG. 1.

Other eyebrow treatment templates are shown in FIGS. 2 and 3 at 20 and 30, respectively, each having a respective opening 22 and 32 formed therein. It will be seen that the shape and size of the openings 22 and 32 are different one from the other, and differ from the symmetrical and mirror imaged openings 16, 18 shown in FIG. 1.

Figure 4:
FIG. 4 shows a cross-section of a typical template having a single coating placed on a substrate.

Referring to FIG. 4, a substrate 40 is shown, having a coating 42 on one side thereof.

Figure 5:
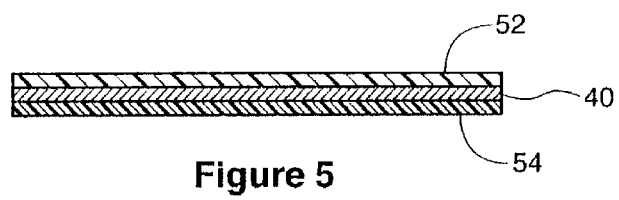
FIG. 5 is a cross-section of a single template having coatings placed on both sides of a substrate.

In FIG. 5, a substrate 40 has coatings 52 and 54, one on each side thereof.

It can be appreciated that if any of the eyebrow treatment templates 12, 14, 20, 30, are intended for use as an eyebrow shaping template for applying to the eyebrow area of the human face so as to define an area for colouring a desired shape of a left or right eyebrow, then one side of a substrate 40 will have a low-tack non-allergenic adhesive coating applied thereto. FIG. 4 suggests such a structure, where in this case, the coating layer 42 is a low-tack non-allergenic adhesive coating. Of course, such coating, and the material of the substrate, will be of the sort which are approved by the FDA for use in the area of the eye in contact with the skin surrounding the eye.

Clearly, any particular shape which is desired may be chosen by the user, oftentimes in consultation with a cosmetician or beautician, or otherwise with a cosmetic or make-up specialist or consultant.

It is also clear that if the adhesive coating is on the upper side of the templates 20 or 30 as seen in FIGS. 2 and 3, those templates would be used for treatment of the left eyebrow.

Because the shape of the forehead in the region of the eyebrow is not flat, either vertically or horizontally, it is important for the substrate 40 to be flexible. Also, because a shape 16, 18, 22, or 32, may be specifically chosen as being the correct (or desired) shape for that individual for whom the eyebrow treatment template is to be used, the material of the substrate should be non-stretchable, so as to be able to maintain its shape and the shape of the opening 16, 18, 22, or 32, when the eyebrow treatment template 12, 14, 20, or 30, is in use.

Typically, the material of the substrate is a material which is flexible and non-stretchable, and is typically a material which is the same as that which is used for surgical tape. Indeed, surgical tape may be employed for the purposes of use in the eyebrow treatment templates of the present invention. Other suitable materials include paper, vinyl, cellulose, polyethylene, tightly woven synthetic fibres, tightly woven natural fibres, and combinations and mixtures thereof.

Because it is usually intended to treat both eyebrows at the same time, typically the eyebrow treatment templates of the present invention are provided in sets, each having a desired shape for both a left eyebrow and a right eyebrow. Such a set is shown in FIG. 1.

If the adhesive coating is on the underside of a pair of templates 12, 14, as seen in FIG. 1, then template 12 is for use with the right eye and template 14 is for use with the left eye.

Also, referring to FIG. 1, a pair of eyebrow treatment templates 12, 14 may be one of a plurality of similar pairs. Each template has a first end 60 and a second end 62. A plurality of pairs of eyebrow treatment templates 12, 14 may be formed into a roll, for dispensing one pair of eyebrow shaping templates at a time. Typically, the eyebrow treatment template sets which comprise a pair of templates 12, 14 are removably attached one to another at their respective first and second ends 60, 62, by perforations formed through the material of the eyebrow treatment template. Moreover, the templates 12 and 14 in a set 10 thereof may, themselves, be separable at a perforation 64, because the spacing between the eyebrows—and therefore, the placement where the openings 16, 18 are to be put—will vary from person to person.

Typically, when the eyebrow treatment templates of the present invention are formed into a roll, a release film (not shown) is placed over the low-tack non-allergenic adhesive coating, such as by being placed over the coating 42 as seen in FIG. 4.

If the eyebrow treatment templates of the present invention are to be used as eyebrow shaping templates, and are formed on a substrate against which a release film is placed over the adhesive coating, then the chad which is formed by a stamping process may be maintained in place against the release film. That chad may, in some circumstances, find usefulness so that it can be removed and applied to an eyebrow for masking the eyebrow when a further procedure—such as depilation, or the placement of foundation makeup on the skin in the region of the eyebrow, is to follow, and where it is desirable that the depilatory composition which may be used, or the foundation make-up which is to be used, does not contact the eyebrow. Thus, the chad can be used to mask the eyebrow in such circumstances.

As discussed above, an eyebrow treatment template in keeping with the present invention may also be used as an eyebrow waxing template. In that case, however, a depilatory coating is placed on the surface of the substrate, in the area surrounding the opening which has the shape of the eyebrow. Thus, the shape of the eyebrow opening 16, 18, 22, or 32, is that shape of the eyebrow which is to remain after a depilation procedure has been carried out.

As is known, depilation involves intimately associating a depilatory composition with the unwanted hair so that the hair adheres to the depilatory composition, and then removing the depilatory composition away from the skin, whereby the hair is essentially yanked out of the skin by its roots. However, if the depilation procedure is skilfully carried out, and the correct depilatory composition is used, there may be little pain and/or irritation, redness, or swelling occur during and following the depilation procedure.

Accordingly, if a depilatory coating is employed in the place of the coating 42 in FIG. 4, then an eyebrow waxing template has been made. Its use is otherwise as described above, except that its purpose is as an eyebrow waxing template.

That means that the depilatory coating must be one which can be activated at the time when it is intended for the depilation procedure to take place. The depilatory coating may be heat-activated, or it may be pressure-activated. If the depilatory coating is a heat-activated composition, then it will be exposed to heat just prior to the depilation procedure, and is put into place such that the opening 16, 18, 22, or 32, is in place over the left or right eyebrow which can be seen therethrough. Thus, the depilatory coating—such as is shown at 42 in FIG. 4—is in contact with the skin and with any unwanted hair in the region of the eyebrow which is away from the opening in the template.

The precise chemical formulation of the depilatory compositions that may be employed on eyebrow waxing templates in keeping with the present invention, is outside the scope of the present invention. However, typical heat-activated depilatory compositions may include a low melting point depilatory wax that includes a naturally occurring resinous substance. It may also include a low melting point depilatory wax which includes paraffin wax; or a low melting depilatory wax which includes beeswax; or a low melting depilatory wax which includes sucrose and maltodextrin. Of course, mixtures thereof may also be employed.

To activate the heat-activated depilatory composition, the eyebrow waxing template may be temporarily exposed to a source of radiant heat such as by placing it under a heat lamp, or it may be temporarily placed in contact with steam or a heated liquid such as hot water or heated alcohol compositions. In any event, typically the heat-activated depilatory composition is one which becomes softened so as to adhere to the unwanted hairs in the area where the depilatory coating is to be placed, at temperatures in the range of 50° C. to 65° C., so as not to be too warm when put into contact with the skin of the face in the eyebrow region.

A pressure-sensitive depilatory composition may also be employed, which is such that when the template 12, 14, 20, or 30, is put into place and pressure is applied against the template, the depilatory composition becomes somewhat softened and activated for use in a depilation procedure. Such pressure-activated depilatory compositions include styrene-isoprene-styrene copolymers, hydrogenated rosins, and depilatory jellies which include a starch syrup, or mixtures thereof.

As before, the eyebrow waxing templates of the present invention may be provided in pairs, and in rolls.

Finally, as particularly shown in FIG. 5, an eyebrow treatment template in keeping with the present invention may serve the purposes of both an eyebrow shaping template and an eyebrow waxing template. To that end, therefore, a structure as shown in FIG. 5 is employed, where the substrate 40 has a low-tack non-allergenic adhesive coating 52 on the first or upper side thereof, and a depilatory coating 54 on the second or lower side thereof.

Depending on which side of the eyebrow shaping and waxing template is to be employed, the template will function as either an eyebrow shaping template or an eyebrow waxing template, in the manner described above. However, the eyebrow shaping and waxing templates of the present invention are such that when one procedure is completed, each template may be turned over for the other procedure to be conducted for the other eyebrow.

Typically, that means that a depilation procedure might first be carried out, whereby unwanted hair is removed, followed by an eyebrow shaping or colouring procedure whereby eyebrow pencil, powder, or other suitable eyebrow colouring cosmetic may be employed.

As before, the eyebrow shaping and waxing templates of the present invention are typically provided in sets or pairs, or rolled in plurality of pairs of templates.

There has been described an eyebrow treatment template which may be employed for purposes of shaping the eyebrow and colouring a desired shape on the face of the user, or which may be employed for purposes of depilation of unwanted hair by an eyebrow waxing template, or which may be employed for either purpose depending on which side of a substrate having an adhesive coating and a depilatory coating is employed against the skin in the region of the eyebrow for the respective procedure to be followed.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Other modifications and alterations maybe used in the design and manufacture of the apparatus of the present invention without departing from the spirit and scope of the accompanying claims.

What is claimed is:

1. An eyebrow shaping template set for defining and colouring a desired shape of both a left and a right eyebrow on a human face, said eyebrow shaping template set comprising of eyebrow shaping templates, each of which comprises:

a substrate, having a first side and a second side;

a low-tack non-allergenic adhesive coating on one of said first and second sides of said substrate, for temporary adhesion to the skin of the human face; and an opening formed through said adhesive coating and said substrate, the shape of said opening being said desired shape for a left eyebrow or a right eyebrow;

wherein said substrate is flexible; and wherein said substrate is non-stretchable, so as to maintain its shape and the shape of the opening therein when in use;

wherein one of said pair of templates has an opening formed therein for colouring a left eyebrow when placed in the left eyebrow area of a human face with the adhesive coating thereon in contact with the skin of the face, and the other of said pair of templates has an opening formed therein for colouring a right eyebrow when placed in the right eyebrow area of a human face with the adhesive coating thereon in contact with the skin of the face;

wherein said pair of eyebrow shaping templates is one of a plurality of similar pairs of eyebrow shaping templates, each having first and second ends, which are removably attached one to another at their respective first and second ends; and wherein said plurality of pairs of eyebrow shaping templates are formed into a roll thereof, for dispensing one pair of eyebrow shaping templates at a time.

2. The eyebrow shaping template set of claim 1 wherein each of said pair of eyebrow shaping templates has an opening formed therein which is chosen from a plurality of different shapes for colouring different shaped eyebrows.

3. The eyebrow shaping template of claim 1, wherein said substrate is chosen from the group consisting of surgical tape, paper, vinyl, cellulose, polyethylene, tightly woven synthetic fibres, and combinations and mixtures thereof.

4. The eyebrow shaping template set of claim 1, further comprising a release film placed over said low-tack non-allergenic adhesive coating.

5. The eyebrow shaping template set of claim 4, wherein said opening formed in each eyebrow shaping template has been formed by stamping, whereby a chad is formed in the shape of said opening; and wherein said chad is adhered to said release film, for removal and application to an eyebrow for masking the eyebrow when further procedures will follow in the region surrounding the eyebrow.

6. An eyebrow waxing template for depilation of an area surrounding a left or right eyebrow on the human face, said eyebrow waxing template comprising:

a substrate, having a first side and a second side;

a depilatory coating on one of said first and second sides of said substrate, for placement against the skin and any unwanted hair in the eyebrow region of a human face; and an opening formed through said depilatory coating and said substrate, said opening having a desired shape of a left eyebrow or a right eyebrow to remain in the eyebrow area of a human face following a depilation procedure;

wherein said substrate is flexible, and is non-stretchable so as to maintain its shape and the shape of the opening therein when in use; and wherein said depilatory coating is chosen from the group consisting of heat-activated depilatory compositions, pressure-activated depilatory compositions, and combinations thereof.

7. An eyebrow waxing template set for depilation of the areas surrounding each of the left eyebrow and the right eyebrow of a human face, said eyebrow waxing template set comprising a pair of eyebrow waxing templates as claimed in claim 6, wherein one of said pair of templates has an opening therein for placement over the left eyebrow of a human face during a depilation procedure in the region of the left eyebrow; and the other of said pair of templates has an opening therein for placement over the right eyebrow of a human face during a depilation procedure in the region of the right eyebrow.

8. The eyebrow waxing template set of claim 7, wherein each of said pair of eyebrow waxing templates has an opening formed therein which is chosen from a plurality of different shapes for use during any depilation procedure in the region of left and right eyebrows, each having a desired shape.

9. The eyebrow waxing template of claim 6, wherein said substrate is chosen from the group consisting of surgical tape, paper, vinyl, cellulose, polyethylene, tightly woven synthetic fibres, tightly woven natural fibres, and combinations and mixtures thereof.

10. The eyebrow waxing template set of claim 7, wherein said pair of eyebrow waxing templates is one of a plurality of similar pairs of eyebrow waxing templates, each having first and second ends, which are removably attached one to another at their respective first and second ends; and wherein said plurality of pairs of eyebrow waxing templates are formed into a roll thereof, for dispensing one pair of eyebrow waxing templates at a time.

11. The eyebrow waxing template of claim 6, wherein said depilatory coating is chosen from the group of heat activated depilatory compositions consisting of a low melting point depilatory wax which includes a naturally occurring resinous substance, a low melting point depilatory wax which includes paraffin wax, a low melting depilatory wax which includes beeswax, a low melting depilatory wax which includes sucrose and maltodextrin, and mixtures thereof, wherein said depilatory coating is heat activatable by being temporarily exposed to a source of radiant heat, or by being placed in contact with steam or a heated liquid; or from the group of pressure sensitive depilatory compositions consisting of styrene-isoprene-styrene copolymers, hydrogenated rosins, depilatory jellies which include a starch syrup, and mixtures thereof.

12. An eyebrow shaping and waxing template for conducting either of an eyebrow colouring procedure to either of the left eyebrow or the right eyebrow of a human face, or a depilation procedure of the hair surrounding the eyebrow in the region of the right eyebrow or the left eyebrow of a human face, said eyebrow shaping and waxing template comprising:

a substrate, having a first side and a second side;

a low-tack non-allergenic adhesive coating on said first side of said substrate, for temporary adhesion to the skin of the human face; and a depilatory coating on said second side of said substrate, for placement against the skin and any unwanted hair in the eyebrow region of a human face;

an opening formed through said adhesive coating, said substrate, and said depilatory coating, said opening having a desired shape of an eyebrow area to be coloured or of the eyebrow to be left in the eyebrow area of a human face following a depilation procedure;

wherein said substrate is flexible, and is non-stretchable so as to maintain its shape and the shape of the opening therein when in use; and wherein said depilatory coating is chosen from the group consisting of heat-activated depilatory compositions, pressure-activated depilatory compositions, and combinations thereof.

13. An eyebrow shaping and waxing template set for colouring a desired shape of both a left and a right eyebrow on a human face, or for depilation of the areas surrounding each of the left eyebrow and the right eyebrow of a human face, said eyebrow shaping and waxing template set comprising a pair of eyebrow shaping and waxing templates as claimed in claim 12, wherein one of said pair of eyebrow shaping and waxing templates has an opening formed therein for colouring a left eyebrow when placed in the left eyebrow area of a human face with said adhesive coating on the first side of said substrate being in contact with the skin of the face, or for placement over the right eyebrow of a human face during a depilation procedure in the region of the right eyebrow when said depilatory coating on the second side of said substrate is placed against the skin and any unwanted hair in the right eyebrow region of a human face; and wherein the other of said pair of eyebrow shaping and waxing templates has an opening formed therein for colouring a right eyebrow when placed in the right eyebrow area of a human face with said adhesive coating on the first side of said substrate being in contact with the skin of the face, or for placement over the left eyebrow of a human face during a depilation procedure in the region of the left eyebrow when said depilatory coating on the second side of said substrate is placed against the skin and any unwanted hair in the left eyebrow region of a human face.

14. The eyebrow shaping and waxing template set of claim 13, wherein each of said eyebrow shaping and waxing templates has an opening formed therein which is chosen from a plurality of different shapes for colouring different shaped eyebrows, or for use during any depilation procedure in the region of left and right eyebrows, each having a desired shape.

15. The eyebrow shaping and waxing template of claim 12, wherein said substrate is chosen from the group consisting of surgical tape, paper, vinyl, cellulose, polyethylene, tightly woven synthetic fibres, tightly woven natural fibres, and combinations and mixtures thereof.

16. The eyebrow shaping and waxing template set of claim 13, wherein said pair of eyebrow shaping and waxing templates is one of a plurality of similar pairs of eyebrow shaping and waxing templates, each having first and second ends, which are removably attached one to another at their respective first and second ends; and wherein said plurality of pairs of eyebrow shaping and waxing templates are formed into a roll thereof, for dispensing one pair of eyebrow shaping and waxing templates at a time.

17. The eyebrow shaping and waxing template set of claim 16, further comprising a release film placed over said low-tack non-allergenic adhesive coating.

18. The eyebrow shaping and waxing template of claim 12, wherein said depilatory coating is chosen from the group of heat activated depilatory compositions consisting of a low melting point depilatory wax which includes a naturally occurring resinous substance, a low melting point depilatory wax which includes paraffin wax, a low melting depilatory wax which includes beeswax, a low melting depilatory wax which includes sucrose and maltodextrin, and mixtures thereof, wherein said depilatory coating is heat activatable by being temporarily exposed to a source of radiant heat, or by being placed in contact with steam or a heated liquid; or from the group of pressure sensitive depilatory compositions consisting of styrene-isoprene-styrene copolymers, hydrogenated rosins, depilatory jellies which include a starch syrup, and mixtures thereof.

\* \* \* \* \*